(12) United States Patent
Harichian et al.

(10) Patent No.: US 6,696,069 B2
(45) Date of Patent: Feb. 24, 2004

(54) SKIN CARE COSMETIC COMPOSITIONS CONTAINING PHOSPHATES AND/OR SULFATES OF BRANCHED ALCOHOLS AND/OR ETHOXYLATES THEREOF

(75) Inventors: Bijan Steven Harichian, Warren, NJ (US); Laurence Boen, Wayne, NJ (US); John Steven Bajor, Ramsey, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 55 days.

(21) Appl. No.: 09/873,065

(22) Filed: Jun. 1, 2001

(65) Prior Publication Data
US 2002/0041890 A1 Apr. 11, 2002

Related U.S. Application Data

(60) Provisional application No. 60/215,431, filed on Jun. 30, 2000.

(51) Int. Cl.$^7$ .................. A61K 7/00; A61K 31/07; A61K 7/48
(52) U.S. Cl. ............... 424/401; 514/725; 514/864; 514/859; 510/159
(58) Field of Search ................ 424/401; 514/725, 514/864, 859; 510/159

(56) References Cited

U.S. PATENT DOCUMENTS

| 3,992,443 A | | 11/1976 | Springmann ............... 260/535 |
| 5,093,112 A | | 3/1992 | Birtwistle .................... 424/70 |
| 5,344,850 A | | 9/1994 | Hata et al. .................. 514/739 |
| 5,447,652 A | * | 9/1995 | Nozaki et al. ......... 252/174.16 |
| 5,756,109 A | | 5/1998 | Burger et al. ................ 424/401 |
| 5,837,728 A | * | 11/1998 | Purcell ....................... 514/529 |
| RE36,068 E | * | 1/1999 | Klgman ....................... 514/381 |
| 6,020,303 A | | 2/2000 | Cripe et al. ................. 510/503 |
| 6,136,330 A | * | 10/2000 | Soliman et al. ............. 424/401 |
| 6,335,312 B1 | * | 1/2002 | Coffindaffer et al. ....... 510/159 |

FOREIGN PATENT DOCUMENTS

| DE | 199 39 565 A1 | 2/2001 |
| DE | 199 54 830 C1 | 3/2001 |
| EP | 0 491 472 A2 | 6/1992 |
| EP | 0 646 371 A1 | 4/1995 |
| WO | 99/18928 | 4/1999 |

OTHER PUBLICATIONS

Westfechtel et al. (May 3, 2001), DE 19954830 C1.*
International Search Report PCT/EP 01/06374, dated Apr. 12, 2002, 7 pp.
Co-pending application: Harichian et al. S/N: 60/215,573, Filed: Jun. 30, 2000.

* cited by examiner

*Primary Examiner*—Sreeni Padmanabhan
*Assistant Examiner*—Gina C. Yu
(74) *Attorney, Agent, or Firm*—Ellen Plotkin

(57) ABSTRACT

Cosmetic skin care methods and compositions containing phosphates and/or sulfates of branched alcohols and/or ethoxylates thereof. The inventive compositions provide control of sebum secretion from sebocytes, improved oil control and improved skin feel, prevent shine and stickiness, while also providing anti-aging benefits which results in reduced appearance of wrinkles and aged skin, improved skin color, treatment of photoaged skin, improvement in skin's radiance and clarity and finish, and an overall healthy and youthful appearance of the skin.

3 Claims, No Drawings

SKIN CARE COSMETIC COMPOSITIONS CONTAINING PHOSPHATES AND/OR SULFATES OF BRANCHED ALCOHOLS AND/OR ETHOXYLATES THEREOF

This application claims the benefit of provisional application 60/215,431 filed Jun. 30, 2000

FIELD OF THE INVENTION

Cosmetic methods and compositions for conditioning human skin by topical application to the skin of cosmetic compositions containing phosphates and/or sulfates of branched alcohols and/or ethoxylates thereof.

BACKGROUND OF THE INVENTION

Sebum is skin oil which is produced by sebocytes (cells of the sebaceous glands in the skin) and is then secreted to the skin surface. A frequent and undesirable skin condition is "oily skin," the condition which results from the excessive amount of sebum on the skin. Oily skin is associated with a shiny, undesirable appearance and a disagreeable tactile sensation and affects various age groups. Therefore, cosmetic products which provide both sebum control and anti-aging benefits are highly desirable.

The prior art discloses branched alcohols as compounds which provide skin benefits such as sebum suppression. For example, U.S. Pat. No. 5,756,109 issued to Burger et al. (hereinafter "Burger '109") teaches the use of a noncylic polyunsaturated diterpene alcohol, geranyl geraniol, in combination with a retinol as a skin conditioning composition. Burger '109 discloses sebum suppression as one advantage of the branched alcohol in combination with retinol. U.S. Pat. No. 5,344,850 issued to Hata et al. discloses topical compositions containing $C_{18}$ saturated or unsaturated alcohol with four methyl branches for treating or preventing acne.

A problem exists in that branched alcohols alone inherently possess an unpleasant odor, characteristic of vinyl or a "new car smell," making application in cosmetic skin conditioning compositions highly undesirable. Moreover, branched alcohols themselves are water-insoluble.

Derivatives of branched alcohols have also been disclosed in the prior art for a variety of uses, such as personal cleansing compositions. For example, WO 9918928 assigned to The Proctor & Gamble Company, discloses personal cleansing compositions comprising branched surfactant systems having a hydrophobic group and a hydrophilic group. The hydrophobic group comprises mid-chain branched and linear surfactant compounds. The hydrophilic group is selected from the group consisting of sulfate and/or ethoxylates thereof.

U.S. Pat. No. 6,020,303 issued to Cripe et al. (hereinafter "Cripe '303") discloses detergent surfactant compositions derived from mid-chain branched primary alkyl hydrophobic groups and hydrophilic groups. Specifically, Cripe '303 discloses alkyl sulfates for application in laundry and cleaning compositions.

U.S. Pat. No. 5,093,112 issued to Birtwistle et al. discloses topical cleansing (detergent) compositions containing an alcohol and an alkyl or alkenyl phosphate salt.

U.S. Pat. No. 3,992,443 issued to Springmann (hereinafter "Springmann '443") discloses a process for the carboxymethylation of alcohols or ether alcohols in a single stage. Springmann '443 teaches the use of both straight chain and branched alcohols as suitable starting alcohols.

The prior art cited above does not seem to suggest or disclose cosmetic compositions or methods for skin conditioning which avoid the negative characteristics of branched alcohols. Therefore, a need remains for cosmetic compositions that retain the beneficial effects of branched alcohols in relation to sebum suppression and skin conditioning while avoiding the unpleasant odor and water-insolubility associated with such alcohols.

SUMMARY OF THE INVENTION

The present invention includes a skin care cosmetic composition comprising:

(i) from about 0.001% to about 50% of a compound of the formula A:

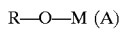

wherein:
R is a branched alkyl chain having at least 9 carbon atoms, generally from 9 to 15 atoms, and at least two branches;
O is an oxygen atom; and
M is ($-SO_3X$), ($-(CH_2CH_2O)_n-SO_3X$), ($-PO_3X$), or ($-(CH_2CH_2O)_n-PO_3X$), and mixtures thereof, where n is an integer of at least 1 and X is hydrogen or a cation;

(ii) a retinoid; and (iii) a cosmetically acceptable vehicle.

The present invention also includes a cosmetic method of controlling or preventing an oily skin condition, especially in the facial area, by applying to the skin the inventive composition.

The invention also includes a cosmetic method of reducing, preventing or controlling sebum secretion from sebocytes by applying the inventive composition.

The invention also includes a cosmetic method of stimulating collagen synthesis by fibroblasts in the skin, by applying to the skin the inventive composition. The inventive methods and compositions provide control of sebum secretion from sebocytes, improved oil control and improved skin feel, and prevent shine and stickiness, while also providing anti-aging benefits which results in reduced appearance of wrinkles and aged skin, improved skin color, treatment of photoaged skin, improvement in skin's radiance and clarity and finish, and an overall healthy and youthful appearance of the skin.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the oil-in-water emulsion, unless otherwise specified.

The term "skin" as used herein includes the skin on the face, neck, chest, back, arms, hands, legs, and scalp.

The inventive methods and compositions include a sulfate or phosphate of a branched alcohol, and/or ethoxylates thereof (sometimes referred to as branched alcohol surfactants and hereinafter "compound A"), and are of the general formula A:

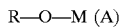

wherein:
R is a branched alkyl chain having at least 9 carbon atoms, generally from 9 to 15 atoms, and at least two branches;
O is an oxygen atom; and
M is (—$SO_3X$), (—($CH_2CH_2O$)$_n$—$SO_3X$), (—$PO_3X$), or (—($CH_2CH_2O$)$_n$—$PO_3X$), and mixtures thereof, where n is an integer of at least 1 and X is hydrogen or a cation. The cation is selected from the group consisting of sodium, lithium, potassium, calcium, magnesium, and amines including quartenary alkyl amines.

The branched alkyl chain of the present invention is derived from a branched alcohol having at least 9 carbon atoms and at least two branches. As seen in Example 1 discussed infra, alcohols with less than 9 carbons do not aid in collagen synthesis. The preferred alcohols from which the inventive compositions are derived, contain a total of at least 10 carbon atoms in order to obtain maximum efficacy. The most preferred alcohols from which the inventive compositions are derived, contain from 2 to 5 branches, in order to maximize efficacy at minimum cost. Preferably, the branches are methyl branches, due to commercial availability. The alcohol may contain a mix of various chain lengths' alcohols. Such mixed alcohol is suitable in deriving the inventive compositions, as long as the predominant alcohol in the mix contains a total of at least 9 carbon atoms and at least two branches.

Sulfation of the branched alcohol involves the addition of a sulfate group to the branched alcohol. Phosphorylation of the branched alcohol involves the addition of a phosphate group to the branched alcohol. Compound A is derived from alcohols which are commercially available, e.g. from Exxon or Henkel.

Ethoxylation involves first directly adding an ethylene oxide to the branched alcohol, followed by either sulfation of phosphorylation.

The salt forms of compound A (where M is a cation in formula A) provide a neutral pH for the inventive compositions before application to the skin to avoid irritation and are therefore preferred. Moreover, the salts dissociate upon contact with the skin to release the beneficial characteristics of the anionic nature of the inventive compositions. Preferably, sodium salt is used because of commercial availability.

Compound A of the present invention retains the beneficial sebum suppression qualities of branched alcohols while eliminating the unpleasant odor. Moreover, compound A is an anionic surfactant, thus providing a negative charge that aids in binding the surfactant onto the skin's surface. The water soluble characteristic effectuates delivery into the skin.

Compound A is employed in the inventive methods and compositions in an amount of from 0.001% to about 50%, preferably from 0.1% to 20%, most preferably from 0.1% to 10%.

The inventive compositions containing compound A also include a retinoid.

Retinoids increase collagen synthesis by dermal fibroblasts. This results in protection from sun damage and smoothening of wrinkled skin. Addition of retinoids to compound A provided improved inhibition of lipogenesis as well as increased collagen synthesis in comparison to compound A alone. The term "retinoids" as used herein includes retinoic acid, retinol, retinal, and retinyl esters. Included in the term "retinoic acid" are 13-cis retinoic acid and all-trans retinoic acid.

The term "retinol" as used herein includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol, 9-cis-retinol. Most preferred is all-trans-retinol, due to its wide commercial activity.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate, retinyl lactate, retinyl glycolate, retinyl hydroxy caprylate, retinyl hydroxy laurate, retinyl tartarate.

The retinoids in the present invention are present in an amount of from 0.001% to 10%, preferably from 0.01% to 1%, and most preferably from 0.01% to 0.05%.

Compound A employed in the inventive methods and compositions may be in liquid form, and thus the invention is effective even in the absence of the carrier. However, the compositions according to the invention comprise a cosmetically acceptable vehicle to act as a diluant, dispersant or carrier of compound A thereof, so as to facilitate their distribution when the composition is applied to the skin.

The vehicle may be aqueous, anhydrous or an emulsion. Preferably, the compositions are aqueous or an emulsion, especially water-in-oil or oil-in-water emulsion. Water when present will be in amounts which may range from 5 to 99%, preferably from 40 to 90%, optimally between 60 and 90% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 and 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterols esters, of which cholesterol fatty acid esters are examples thereof.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively, the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Various types of additional active ingredients may be present in cosmetic compositions of the present invention. Actives are defined as skin benefit agents other than emollients and other than ingredients that merely improve the physical characteristics of the composition. Although not limited to this category, general examples include additional anti-sebum ingredients such as talcs and silicas, and sunscreens.

Sunscreens include those materials commonly employed to block ultraviolet light. Illustrative compounds, are the derivatives of PABA cinnamate and salicylate. For example, avobenzophenone (Parsol 1789®) octyl methoxycinnamate and 2-hydroxy4-methoxy benzophenone (also known as oxybenzone) can be used. Octyl methoxycinnamate and 2-hydroxy4-methoxy benzophenone are commercially available under the trademarks, Parsol MCX and Benzophenone-3, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

The composition according to the invention is intended primarily as a product for topical application to human skin, especially as an agent for controlling or preventing excessive sebum secretion.

In use, a quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging:

The cosmetic skin composition of the invention can be in any form, e.g. formulated as a toner, gel, lotion, a fluid cream, or a cream. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,057, incorporated by reference herein.

The following specific examples further illustrate the invention, but the invention is not limited thereto.

The following alcohols used in the Examples were obtained from Exxon:

| Trade Name | Branching |
| --- | --- |
| Exxal ® 7 | Mixture of branched and straight chain isomers, about 40% dimethyl pentanols. |
| Exxal ® 8 | Methyl branching only, at least about 38% dimethyl hexanols. |
| Exxal ® 10 | Trimethyl heptanols and dimethyl octanols |
| Exxal ® 12 | Trimethyl nonanols |
| Exxal ® 13 | Tetramethyl nonanols and trimethyl decanols |

EXAMPLE 1

This example measured production of procollagen I by fibroblasts in response to treatment with various straight chain and branched alcohols alone.

Collagen is a predominant skin protein. Its synthesis decreases with aging or photodamage. The degradation or destruction of collagen increases the tensile strength of the skin causing wrinkles and laxity. Many studies involving human subjects have shown that collagen type I is decreased with increasing severity of photodamage (See Kligman, A., JAMA, (1969), 210, pp. 2377–2380; Lavker, R., J. Inv. Derm., (1979), 73, 79–66; Smith J. et al., J. Inv. Derm., (1962), 39, pp. 347–350; and Shuster, S. et al., Br. J. Dermatol., (1975), 93, pp. 639–643); and some correlation in the histology of wrinkles and reduction in collagen levels in the sun-exposed skin has been reported. See Chen, S.; Kiss, I., J. Inv. Derm., (1992), 98. pp. 248–254. Voorhees and colleagues have supported these findings by showing the restoration of collagen type I in photo-damaged human skin by a topical treatment with tretinoin. See Christopher, E., et al., The New Eng. Jou. of Medicine (1993), 329, pp. 530–535. Procollagen I is a precursor of collagen. Increased production of procollagen I in response to a test compound application is a marker of an increased collagen level.

Procollagen I Staining Protocol for Slot Blot

Neonatal human dermal fibroblasts were purchased from Clonetics Corp., San Diego, Calif. All materials for cell culture were purchased from Life Technologies, NY (and used in passages 5–10). Cells were seeded at a density of approximately 10,000/well in the inner 48 wells of a 96-well plate in a medium containing DMEM (Dulbecco's Modified Eagle's Medium), high-glucose supplemented with 2 mM L-glutamine, 10% fetal bovine serum, and antibiotic and antimycotic solutions. Cells were then grown to confluence for 2 days. At confluence, the medium was removed and cells were washed with serum-free DMEM, and each well dosed with 200 $\mu$l of a solution of a test compound in serum-free DMEM. Each dosing was replicated in a total of six wells. Test compounds were used at concentrations indicated in Table 1 below. Control did not contain a test compound. After 24 hours, the test compound solution or the control solution was removed and cells redosed with 100 $\mu$l of a solution of a test compound in serum-free DMEM.

Nitrocellulose membrane and 3 sheets of filter paper were soaked in TRIS buffered saline (TBS, pH 7.3.). BioRad slot blot apparatus (BioRad Labs, CA) was set up with 3 sheets filter paper on bottom, membrane on top, and tightened. 100 ml TBS was added per well. Vacuum was used to suck TBS through membrane. The test compound solution or control was vortexed, then 100 $\mu$l was loaded per well and gravity filtered. Procollagen from the test solution was bound to the membrane at this point in the procedure. Membrane was removed from the apparatus, excess cut off, and bottom right corner notched for orientation. The membrane was placed in blocking solution (5% milk powder in Dulbecco's phosphate buffered saline) overnight at 4° C., with shaking. The membrane was then incubated for 1.5 hrs at room temperature with 1.5 mL Rat Anti-Human Procollagen Amino-Terminal Ab (Chemicon MAB1912) in TBS with 0.1% BSA (Bovine Serum Albumin) (ratio of antibody to buffer/BSA was 1:100) in a sealed bag with shaking. The membrane was then removed; washed 3 times for 5 minutes in TBS/0.1% Tween. The membrane was then incubated for 1 hour at room temperature in 2 mL of Biotinylated Anti-Rat Peroxidase-Conjugated Ab (Vector Labs) in TBS with 0.1% BSA (ratio of antibody to buffer/BSA was 1:1000) in a sealed bag with shaking. The membrane was then stained using the following solution:

12.5 mg 3-amino 9-ethyl carbazole (Sigma)

3.125 (approximately) mL DMF (N,N-dimethylformamide, from Sigma)

21.5 mL 0.2M NaOAc buffer, pH 5.2

12.5 mL $H_2O_2$

The membrane was stained until color developed and the reaction stopped with 2 washes for 10 minutes in tap water. The blot was scanned on a Bio-Rad GS700 Image Analysis densitometer. Percent change from control was calculated from densitometer readings as follows: [(Reading for test compound−Reading for control)/Reading for control]*100. Control has a reading of 100%. Statistical significance (p value) was calculated using student's t-test.

The results that were obtained are summarized in Table 1. TGF-B is a positive control, ensuring the integrity of the assay: transforming growth factor beta is known to increase procollagen I in fibroblasts.

TABLE 1

| Sample | % Increase (+) or % decrease (−−) over control |
| --- | --- |
| Experiment 1 | |
| TGF-B (transforming growth factor-B) | +50* |
| 0.01% Exxal ® 7 | −10* |
| 0.01% Exxal ® 8 | −30* |
| Experiment 2 | |
| TGF-B | +140* |
| 0.01% Exxal ® 10 | +50* |
| 0.01% Exxal ® 12 | +40* |
| 0.01% Exxal ® 13 | +30* |

*Statistically significant at $p < 0.05$

It can be seen from the results in Table 1, that Exxal® 7 and Exxal® 8, which are not within the scope of the invention (i.e., at least a total of 9 carbons in the branched alkyl chain with at least 2 branches), did not increase collagen synthesis by fibroblasts. By contrast, the alcohols (Exxale® 10, Exxal® 12, and Exxal® 13) from which compound A of the present invention is derived, all increased collagen synthesis.

EXAMPLE 2

This example provided sulfation of an alcohol.

In a 50 ml 3-neck round bottom flask fitted with a condensor, stirrer, addition funnel and $N_2$ inlet/outlet device was charged tridecyl alcohol (Exxal® 13) (2.0 g, $10^{-2}$M) dissolved in 10.0 ml dry methylene chloride and the system flushed with $N_2$ for a moisture free atmosphere. While stirring, chlorosulfonic acid (1.17 g, 1.0 M equivalent)

dissolved in 5.0 ml dry methylene chloride was added dropwise. After addition, the resulting reaction solution was stirred overnight at room temperature. The reaction solution became dark due to the brown colored starting chlorosulfonic acid.

After overnight stirring, the reaction solution was rotavaped to dryness to give a dark colored liquid material. Yield was 2.12 g. The $^1$H—NMR (CDCl$_3$) of the colored liquid showed appearance of two multiplets at 4.16 and 3.81 ppm (1.00:1.66 ratio), the latter identified as unreacted starting tridecyl alcohol (by spiking). There was very little odor in the sulfated product.

Half of the sulfated tridedyl alcohol was dissolved in about 75 ml water and neutralized with dilute base (10% base) to pH 7.0. It was observed that a dark oily residue separated from the aqueous phase. This was extracted with methylene chloride in a separatory funnel, which resulted in an emulsion, causing difficulty in obtaining complete separation of the organic phase from the aqeuous phase. Therefore, the following was done: 1). The methylene phase was separated as much as possible and rotavaped to give about 0.34 g dark colored liquid. Its $^1$H—NMR (CDCl$_3$) indicated it to be unreacted starting alcohol (multiplet at 3.63 ppm, corresponding to Exxal® 13). However, this dark residue possessed an odor which was different from the original Exxal® 13 odor 2). The aqueous phase was freeze-dried to give a light brown solid, which picked up moisture and became sticky. Its $^1$H—NMR (D$_2$O) showed a multiplet peak at about 4.05 ppm which is typical of sulfate ester and a minor peak at 3.59 ppm which appeared to be unreacted alcohol. The Na salt was further treated with methylene chloride which dissolved most of the solids, leaving behind a small amount of solids (Na$_2$SO$_4$) and centrifuged. The methylene chloride phase was decanted and removal of methylene chloride gave a light brown solid. Yield was about 0.53 g.

EXAMPLE 3

This example provided phosphorylation of an alcohol.

85% Phosphoric acid (H$_3$PO$_4$) (1.96 g, 0.02 mole) and phosphorus pentoxide (P$_2$O$_5$) (0.95 g, 0.067 mole) were weighed out in a moisture free atmosphere (N$_2$ dry box) to a small 3-neck round bottle flask. Warning: Mixing H$_3$PO$_4$ and P$_2$O$_5$ generated a lot of heat. After mixing well using a mechanical stirrer under N$_2$, iso-tridecanol (Exxal® 13) alcohol (4.0 g, 0.02 mole) was added dropwise over about 20 minutes at 45–50° C. (oil-bath temperature). Before addition was completed, the reaction mixture turned very viscous and became difficult to stir. To this was added 5.0 ml dry cyclohexane which facilitated mixing and completed addition of iso-tridecanol. After addition, the colorless homogeneous reaction mixture was stirred at the same oil-bath temperature overnight under N$_2$. After overnight stirring, the homogeneous mixture turned somewhat brownish. The mixture was allowed to cool to room temperature, and diluted with 25 mL petroleum ether. Water was then added and stirred well, then the two phases allowed to separate in a separatory funnel. The organic layer (upper) was separated and dried (MgSO$_4$). After filtering off the MgSO$_4$, removal of the petroleum ether (rotavap) yielded 3.40 g lightly colored crude liquid product.

$^1$H—NMR analysis indicated a mixture of product (—CH$_2$—OPO multiplet at 4.01 ppm) and unreacted iso-tridecanol (—CH$_2$—OH multiplet at 3.68 ppm). The presence of iso-tridecanol was confirmed by GC analysis of the crude product. The product mono-alkyl (Exxal® 13) phosphate was purified by dissolving the crude product in water and neutralizing with base to pH=9.0 and freeze-dried to recover the Na salt form of the mono-alkyl (Exxal® 13) phosphate. The Na salt was treated with methylene chloride to remove the excess Exxal® 13 alcohol. The purified Na salt product was recovered by centrifugation and decanting the methylene chloride phase (done 2–3 times). After further drying, about 1.0 g sticky solid was obtained. About 0.15 g of the sticky solid was redissolved in water and acidified with HCl and freeze-dried, and the freeze-dried residue extracted with methylene chloride to recover about 0.13 g of the acid form of mono-alkyl (Exxal® 13) phosphate. $^1$H—NMR analysis of the acid and Na salt forms of mono-alkyl (Exxal® 13) phosphate showed them to be free of iso-tridecanol (Exxal® 13), with the acid (—CH$_2$—OPO) multiplet at 4.01 ppm and the Na salt at 3.76 ppm.

EXAMPLE 4

This example provided data on inhibition of sebocyte lipogenesis.

The iso-tridecyl sulfated Exxal® 13 alcohol and sodium salt thereof and the iso-tridecyl phosphorylated Exxal® 13 alcohol and sodium salt thereof were obtained from examples 2 and 3, respectively.

Secondary cultures of human sebocytes obtained from an adult male were grown in 48-well tissue culture plates (Costar Corp.; Cambridge, Mass.) or 96-well tissue culture plates (Packard Co.; Meriden, Conn.) until confluent. Sebocyte growth medium consisted of Clonetics Keratinocyte Basal Medium (KBM) supplemented with 14 $\mu$g/mL bovine pituitary extract, 0.4 $\mu$g/mL hydrocortisone, 5 $\mu$g/mL insulin, 10 ng/mL epidermal growth factor, 1.2×10$^{-10}$ M cholera toxin, 100 units/mL penicillin, and 100 $\mu$g/mL streptomycin. All cultures were incubated at 37° C. in the presence of 7.5% CO$_2$. Medium was changed three times per week.

On the day of experimentation, the growth medium was removed and the sebocytes washed three times with sterile Dulbecco's Modified Eagle Medium (DMEM; phenol red free). Fresh DMEM was added to each sample (duplicates, triplicates, or quadruplicates depending on the experiment) with 5 microliter of test agent solubilized in ethanol or sterile, distilled water either alone or in the presence of one or 10 micromolar of retinol. Controls consisted of addition of ethanol alone sterile, distilled water, retinol alone, sterile, distilled water, or phenol red, which has estrogen-like activity and is included as a positive control.

Each plate was returned to the incubator for 20 hours followed by the addition of $^{14}$C-acetate buffer (5 mM final concentration, 56 mCi/mmol specific activity). Sebocytes were returned to the incubator for four hours after which each culture was rinsed three times with phosphate buffered saline to remove unbound label. Radioactive label remaining in the sebocytes was harvested and counted using a Beckman scintillation counter.

The results that were obtained are summarized in Tables 2–4.

TABLE 2

| Treatment | % of Control |
| --- | --- |
| Control | 100.0 |
| 28 µM Phenol Red | 91.9 |
| 280 µM Phenol Red | 58.1* |
| 35.6 µM Iso-tridecyl Sulfate | 63.5 |
| 178 µM Iso-tridecyl Sulfate | 18.1* |
| 356 µM Iso-tridecyl Sulfate | 7.4* |
| 33.1 µM Iso-tridecyl Sulfate, sodium salt | 54.9* |
| 165.5 µM Iso-tridecyl Sulfate, sodium salt | 14.0* |
| 331 µM Iso-tridecyl Sulfate, sodium salt | 5.5* |

*statistically significant at $p < 0.01$

As shown in Table 2, iso-tridecyl sulfate alone or as a salt, reduced lipogenesis production.

TABLE 3

| Treatment | % of Control |
| --- | --- |
| Control | 100.0 |
| 28 µM Phenol Red | 92.0 |
| 280 µM Phenol Red | 61.7* |
| 1 µM Retinol | 91.8 |
| 10 µM Retinol | 105.7 |
| 1 µM Iso-tridecyl Sulfate | 72.5* |
| 1 µM Iso-tridecyl Sulfate + 1 µM Retinol | 70.6* |
| 1 µM Iso-tridecyl Sulfate + 10 µM Retinol | 64.4* |
| 10 µM Iso-tridecyl Sulfate | 58.2* |
| 10 µM Iso-tridecyl Sulfate + 1 µM Retinol | 56.1* |
| 10 µM Iso-tridecyl Sulfate + 10 µM Retinol | 47.5* |

*statistically significant at $p < 0.01$

As shown in Table 3, iso-tridecyl sulfate in combination with retinol showed improved lipogenesis inhibition in comparison to iso-tridecyl sulfate alone or retinol alone.

TABLE 4

| Treatment | % of Control |
| --- | --- |
| Control | 100.0 |
| 280 µM Phenol Red | 70.6* |
| 1 µM Retinol | 97.4 |
| 10 µM Retinol | 106.0 |
| 1 µM Iso-tridecyl Phosphate (Disodium salt) | 90.7 |
| 1 µM Iso-tridecyl Phosphate + 1 µM Retinol | 78.1* |
| 1 µM Iso-tridecyl Phosphate + 10 µM Retinol | 71.6* |
| 10 µM Iso-tridecyl Phosphate (Disodium salt) | 88.4 |
| 10 µM Iso-tridecyl Phosphate + 1 µM Retinol | 70.6* |
| 10 µM Iso-tridecyl Phosphate + 10 µM Retinol | 66.9* |
| 100 µM Iso-tridecyl Phosphate (Disodium salt) | 88.3 |
| 100 µM Iso-tridecyl Phosphate + 1 µM Retinol | 74.1* |
| 100 µM Iso-tridecyl Phosphate + 10 µM Retinol | 78.2 |

*statistically significant at $p < 0.01$

As shown in Table 4, iso-tridecyl phosphate in combination with retinol enhanced inhibition of lipogenisis production in comparison to iso-tridecyl phosphate alone or retinol alone.

EXAMPLE 5

This example measured production of procollagen I by fibroblasts in response to treatment with various test compounds.

The experiment was conducted as described in Example 1 above. Fold increase was calculated as a ratio of densitometer reading for cells treated with a test compound over control. The results that were obtained are summarized in Table 5:

TABLE 5

| Test Compound | Average OD (optical density) Reading | Standard Deviation | p-value (vs. control) | Fold increase Over Control |
| --- | --- | --- | --- | --- |
| Plate 1 | | | | |
| Control | 0.783 | 0.485 | | |
| 0.001% TGF-b (transforming growth factor-beta) | 1.348 | 0.200 | 0.009 | 1.72 |
| 0.0001% Iso-Tridecyl Sulfate | 1.000 | 0.420 | 0.132 | 1.28 |
| 0.001% Iso-Tridecyl Sulfate | 1.223 | 0.356 | 0.071 | 1.56 |
| Plate 2 | | | | |
| Control | 1.000 | 0.419 | | |
| 0.001% TGF-b (transforming growth factor-beta) | 1.653 | 0.275 | 0.006 | 1.65 |
| 0.0001% Iso-Tridecyl Phosphate | 2.170 | 0.425 | 0.001 | 2.17 |
| 0.001% Iso-Tridecyl Phosphate | 1.460 | 0.447 | 0.012 | 1.460 |

TGF-b was incorporated as a positive control

As shown in Table 5, both iso-tridecyl sulfate and iso-tridecyl phosphate increased collagen production.

| Compound | Chemical Name | Chemical Formula |
|---|---|---|
| Lialet 123-2 | Alcohol, $C_{12}$–$C_{13}$ Poly (2) Ethoxylate | R—(O—$CH_2$—$CH_2$)$_n$OH<br>R = $C_{12}$–$C_{13}$ n = ~2 |
| Lorodac 1-24 | Alcohol, $C_{12}$–$C_{14}$ (1) Ethoxylate | R—(O—$CH_2$—$CH_2$)$_n$OH<br>R = $C_{12}$–$C_{14}$ n = ~1 |
| Daclor 70-1-23 AL | Primary Alcohol $C_{12}$–$C_{13}$ (1) Ethoxylate, Sulfate, Sodium Salt | R—(O—$CH_2$—$CH_2$)$_n$—O—S(=O)$_2$—O$^+$  Na$^+$<br>R = $C_{12}$–$C_{13}$ n = ~1 |
| Dacpon 27-23 | Sulfuric Acid, mono ($C_{12}$–$C_{13}$) alkyl ester, sodium salt | R—O—S(=O)$_2$—O—Na<br>R = $C_{12}$–$C_{13}$ |
| Daclor 70-3-23 AL | Primary Alcohol $C_{12}$–$C_{13}$ Poly (3) Ethoxylate, Sulfate, Sodium Salt | R—(O—$CH_2$—$CH_2$)$_n$—O—S(=O)$_2$—O$^+$  Na$^+$<br>R = $C_{12}$–$C_{13}$ n = ~3 |
| Cosmacol AES 70-2-24 NE | Primary Alcohol $C_{12}$–$C_{13}$ Poly (2) Ethoxylate, Sulfate, Sodium Salt | R—(O—$CH_2$—$CH_2$)$_n$—O—S(=O)$_2$—O$^+$  Na$^+$<br>R = $C_{12}$–$C_{14}$ = ~2 |
| Cosmacol AES 70-3-24 NE | Primary Alcohol $C_{12}$–$C_{14}$ Poly (3) Ethoxylate, Sulfate, Sodium Salt | R—(O—$CH_2$—$CH_2$)$_n$—O—S(=O)$_2$—O$^+$  Na$^+$<br>R = $C_{12}$–$C_{14}$ n = ~3 |

EXAMPLE 6

This example provided data on inhibition of sebocyte lipogenesis.

The experiment was conducted as described in Example 4 above.

TABLE 6

| Treatment | % of Control |
|---|---|
| 1 μM Lialet ® 123-2 | 79.6* |
| 1 μM Lialet ® 123-2 + 1 μM Retinol | 79.0 |
| 1 μM Lialet ® 123-2 + 10 μM Retinol | 94.9 |
| 10 μM Lialet ® 123-2 | 85.1 |
| 10 μM Lialet ® 123-2 + 1 μM Retinol | 81.2 |
| 10 μM Lialet ® 123-2 + 10 μM Retinol | 77.3* |
| 100 μM Lialet ® 123-2 | 37.3* |
| 100 μM Lialet ® 123-2 + 1 μM Retinol | 46.0* |
| 100 μM Lialet ® 123-2 + 10 μM Retinol | 49.2* |
| 28 μM Phenol Red | 79.3 |
| 1 μM Retinol | 93.2 |
| 10 μM Retinol | 101.8 |

*statistically significant at $p < 0.01$

TABLE 7

| Treatment | % of Control |
|---|---|
| 1 μM Lorodac ® 1-24 | 73.4* |
| 1 μM Lorodac ® 1-24 + 1 μM Retinol | 78.3 |
| 1 μM Lorodac ® 1-24 + 10 μM Retinol | 83.8* |
| 10 μM Lorodac ® 1-24 | 74.5* |
| 10 μM Lorodac ® 1-24 + 1 μM Retinol | 76.3* |
| 10 μM Lorodac ® 1-24 + 10 μM Retinol | 70.2* |
| 100 μM Lorodac ® 1-24 | 49.0* |
| 100 μM Lorodac ® 1-24 + 1 μM Retinol | 41.8* |
| 100 μM Lorodac ® 1-24 + 10 μM Retinol | 43.9* |
| 28 μM Phenol Red | 92.0 |
| 280 μM Phenol Red | 61.7* |
| 1 μM Retinol | 91.5 |

*statistically significant at $p < 0.01$

As shown in Table 7, Lorodac® 1–24 inhibited lipogenesis both alone and in combination with retinol.

TABLE 8

| Treatment | % of Control |
|---|---|
| 1 M Daclor ® 70-1-23-Al | 77.5 |
| 1 μM Daclor ® 70-1-23-Al + 1 μM Retinol | 91.8 |
| 1 μM Daclor ® 70-1-23-Al + 10 μM Retinol | 98.8 |
| 10 μM Daclor ® 70-1-23-Al | 80.5 |
| 10 μM Daclor ® 70-1-23-Al + 1 μM Retinol | 74.2 |
| 10 μM Daclor ® 70-1-23-Al + 10 μM Retinol | 86.7 |
| 100 μM Daclor ® 70-1-23-Al | 6.6* |
| 100 μM Daclor ® 70-1-23-Al + 1 μM Retinol | 7.0* |
| 100 μM Daclor ® 70-1-23-Al + 10 μM Retinol | 7.5* |
| 28 μM Phenol Red | 92.0 |
| 280 μM Phenol Red | 61.7* |
| 1 μM Retinol | 91.5 |

*statistically significant at $p < 0.01$

As shown in Table 8, Daclor® 70-1-23-AL reduced production of lipogenesis both alone and in combination with retinol.

TABLE 9

| Treatment | % of Control |
|---|---|
| 1 μM Dapcon ® 27-23 | 74.1 |
| 1 μM Dapcon ® 27-23 + 1 μM Retinol | 80.2 |
| 1 μM Dapcon ® 27-23 + 10 μM Retinol | 79.3 |
| 10 μM Dapcon ® 27-23 | 60.5* |
| 10 μM Dapcon ® 27-23 + 1 μM Retinol | 56.7* |
| 10 μM Dapcon ® 27-23 + 10 μM Retinol | 68.7* |
| 100 μM Dapcon ® 27-23 | 16.1* |
| 100 μM Dapcon ® 27-23 + 1 μM Retinol | 13.2* |
| 100 μM Dapcon ® 27-23 + 10 μM Retinol | 12.3* |
| 28 μM Phenol Red | 84.0 |
| 1 μM Retinol | 91.8 |
| 10 μM Retinol | 105.7 |

*statistically significant at $p < 0.01$

As shown in Table 9, Dapcon® 27-23 inhibited lipogenesis both alone and in combination with retinol.

TABLE 10

| Treatment | % of Control |
|---|---|
| 1 μM Daclor ® 70-3-23-Al | 85.9 |
| 1 μM Daclor ® 70-3-23-Al + 1 μM Retinol | 94.8 |
| 1 μM Daclor ® 70-3-23-Al + 10 μM Retinol | 86.4 |
| 10 μM Daclor ® 70-3-23-Al | 77.5 |
| 10 μM Daclor ® 70-3-23-Al + 1 μM Retinol | 78.1 |
| 10 μM Daclor ® 70-3-23-Al + 10 μM Retinol | 69.5 |
| 100 μM Daclor ® 70-3-23-Al | 4.4* |
| 100 μM Daclor ® 70-3-23-Al + 1 μM Retinol | 4.1* |
| 100 μM Daclor ® 70-3-23-Al + 10 μM Retinol | 3.4* |

*statistically significant at $p < 0.01$

As shown in Table 10, Daclor® 70-3-23-Al inhibited of lipogenesis, both alone and in combination with retinol.

TABLE 11

| Treatment | % of Control |
|---|---|
| 1 μM Cosmacol ® AES 70-2-24 NE | 69.5 |
| 1 μM Cosmacol ® AES 70-2-24 NE + 1 μM Retinol | 73.3 |
| 1 μM Cosmacol ® AES 70-2-24 NE + 10 μM Retinol | 85.9 |
| 10 μM Cosmacol ® AES 70-2-24 NE | 80.2 |
| 10 μM Cosmacol ® AES 70-2-24 NE + 1 μM Retinol | 83.8 |
| 10 μM Cosmacol ® AES 70-2-24 NE + 10 μM Retinol | 79.0 |
| 100 μM Cosmacol ® AES 70-2-24 NE | 3.4* |
| 100 μM Cosmacol ® AES 70-2-24 NE + 1 μM Retinol | 4.5* |
| 100 μM Cosmacol ® AES 70-2-24 NE + 10 μM Retinol | 5.1* |

*statistically significant at $p < 0.01$

As shown in Table 11, Cosmacol® AES 70-2-24 NE inhibited lipogenesis, both alone and in combination with retinol.

TABLE 12

| Treatment | % of Control |
|---|---|
| 1 μM Cosmacol ® AES 70-3-24 NE | 76.5 |
| 1 μM Cosmacol ® AES 70-3-24 NE + 1 μM Retinol | 89.9 |
| 1 μM Cosmacol ® AES 70-3-24 NE + 10 μM Retinol | 79.9 |
| 10 μM Cosmacol ® AES 70-3-24 NE | 78.7 |
| 10 μM Cosmacol ® AES 70-3-24 NE + 1 μM Retinol | 83.1 |
| 10 μM Cosmacol ® AES 70-3-24 NE + 10 μM Retinol | 80.4 |
| 100 μM Cosmacol ® AES 70-3-24 NE | 6.7* |
| 100 μM Cosmacol ® AES 70-3-24 NE + 1 μM Retinol | 5.3* |
| 100 μM Cosmacol ® AES 70-3-24 NE + 10 μM Retinol | 5.4* |

*statistically significant at $p < 0.01$

As shown in Table 12, Cosmacol® AES 70-2-24 NE inhibited lipogenesis, both alone and in combination with retinol.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin care cosmetic composition comprising:
   (i) from about 0.001% by weight to about 50% by weight of a compound of the formula A:

$$R\text{---}O\text{---}M \quad\quad (A)$$

wherein

R is a branched alkyl chain having at least 9 carbon atoms, and at least two branches;

O is an oxygen atom;

M is ($-CH_2CH_2O)_n-PO_3X$.) and n is an integer of at least 1; and

X is hydrogen or a cation selected from the group consisting of sodium, lithium, potassium, calcium, magnesium, and quaternary alkyl amines;

(ii) a retinoid; and (iii) a cosmetically acceptable vehicle.

2. A cosmetic method of reducing oily skin conditions, the method comprising applying to the skin the composition of claim 1.

3. A cosmetic method of reducing sebum secretion from sebocytes, the method comprising applying to the skin the composition of claim 1.

* * * * *